United States Patent [19]

Prasad et al.

[11] Patent Number: 5,440,038

[45] Date of Patent: Aug. 8, 1995

[54] PROCESS FOR THE PURIFICATION OF SUBSTITUTED 4-AMINO-1,2,4-TRIAZINE-5-ONES

[75] Inventors: Vidyanatha A. Prasad, LeaWood; David M. Mayes, Overland Park; Peter E. Newallis, Leawood, all of Kans.; Karl G. Steinbeck, Leverkusen Monheim, Germany

[73] Assignee: Miles Inc., Pittsburgh, Pa.

[21] Appl. No.: 163,466

[22] Filed: Dec. 7, 1993

[51] Int. Cl.⁶ .................................. C07D 253/075
[52] U.S. Cl. ...................................... 544/182
[58] Field of Search ............................ 544/182

[56] References Cited

U.S. PATENT DOCUMENTS

| | | | |
|---|---|---|---|
| 3,671,523 | 6/1972 | Westphal et al. | 260/248 AS |
| 3,752,808 | 8/1973 | Jautelat et al. | 260/249.5 |
| 4,013,649 | 3/1977 | Bogdanowicz, Jr. | 260/248 AS |
| 4,058,526 | 11/1977 | Merz et al. | 544/182 |
| 4,123,253 | 10/1978 | Hack et al. | 71/93 |
| 4,175,188 | 11/1979 | Klenk et al. | 544/182 |
| 4,309,538 | 1/1982 | Schmidt et al. | 544/182 |
| 4,328,340 | 5/1982 | Bonse et al. | 544/182 |

*Primary Examiner*—John M. Ford
*Attorney, Agent, or Firm*—Joseph C. Gil; Lyndanne M. Whalen; Godfried R. Akorli

[57] ABSTRACT

Substituted 4-amino-1,2,4-triazine-5-ones are purified to remove unwanted N-isomers by maintaining the crude product at a temperature of from about 55° C. to about 70° C. in the presence of a hydroxide, preferably an alkali metal hydroxide for at least 0.5 hour.

10 Claims, No Drawings

PROCESS FOR THE PURIFICATION OF SUBSTITUTED 4-AMINO-1,2,4-TRIAZINE-5-ONES

BACKGROUND OF THE INVENTION

The present invention relates to a process for purifying substituted 4-amino-1,2,4-triazine-5-ones by removing unwanted N-isomers.

Substituted 4-amino-1,2,4-triazine-5-ones are known to be useful as herbicides. These herbicides are disclosed, e.g., in U.S. Pat. No. 3,671.523.

Processes for producing these compounds are known. However, these known processes generally yield approximately 94–95% desired compound and an N-isomer content of approximately 4–5%. It would be commercially advantageous to reduce the N-isomer content to achieve as high an active ingredient (A.I.) content as possible.

SUMMARY OF THE INVENTION

It is an object of the present invention to provide a process for removing unwanted N-isomers from substituted 4-amino-1,2,4-triazine-5-ones.

It is also an object of the present invention to provide a process for producing pure substituted 4-amino-1,2,4-triazine-5-ones in higher yields.

It is also an object of the present invention to provide purer substituted 4-amino-1,2,4-triazine-5-ones with reduced N-isomer contents.

These and other objects which will be apparent to those skilled in the art are accomplished by maintaining the substituted 4-amino-1,2,4-triazine-5-ones at a temperature of from about 55° C. to about 80° C. in the presence of a hydroxide, preferably an alkali metal hydroxide such as sodium hydroxide for at least 30 minutes.

DETAILED DESCRIPTION OF THE PRESENT INVENTION

The present invention relates to a process for the purification of substituted 4-amino-1,2,4-triazine-5-ones by removing unwanted N-isomers. This removal is accomplished by heating the compound to be purified in the presence of a hydroxide, preferably, an alkali metal hydroxide.

The substituted 4-amino-1,2,4-triazine-5-ones to be purified in accordance with the present invention are represented by the formula $$\text{(1)}$$

in which

R represents an aliphatic group having from 1–6 carbon atoms, a cycloaliphatic group having from 5 to 6 ring carbon atoms, an araliphatic group having from 6 to 10 ring carbon atoms in the aryl moiety and from 1 to 2 carbon atoms in the aliphatic moiety, or an aryl group having from 6–10 ring carbon atoms;

$R_1$ and $R_2$ each represents hydrogen, or an alkyl group having from 1 to 4 carbon atoms, and $R_3$ represents an alkyl group having from 1 to 4 carbon atoms.

Preferred compounds within formula I are metribuzin and ethyl-metribuzin, i.e., those in which R represents a t-butyl group, $R_1$ represents hydrogen, $R_2$ represents hydrogen and $R_3$ represents a methyl (metribuzin) or ethyl group (ethyl-metribuzin).

The compounds represented by formula I may be produced by known methods. Such methods are disclosed, e.g., in U.S. Pat. Nos. 3,752,808; 4,013,649; 4,123,253; 4,175,188; 4,309,538; and 4,328,340 which are incorporated herein by reference. U.S. Pat. No. 4,328,340, for example, teaches a process in which pivaloyl cyanide is reacted with a carboxylic anhydride to form an intermediate which is then condensed with thiocarbohydrazide. In another method for producing compounds represented by formula I, an α-iminonitrile is reacted with a hydrazine derivative (U.S. Pat. No. 3,752,808).

It has now been found that unwanted isomers present in the crude reaction product may be removed and the percentage of active ingredient thereby improved. Unwanted isomers are removed by treating the crude reaction product with an aqueous solution of a hydroxide, preferably, an alkali metal hydroxide at a temperature of at least 55° C., and more preferably 60° C. An aqueous solution of sodium hydroxide is preferred. The hydroxide solution is generally used in a concentration of at least 5%, preferably from about 10% to about 15%, most preferably about 12.5%.

The isomer removal is generally carried out at a temperature of at least 55° C., preferably from about 55° C. to about 80° C., most preferably at 60° C. The crude reaction product mixture to which the aqueous hydroxide solution has been added is generally maintained at such temperatures for at least 0.5 hours, preferably from about 0.5 to about 3 hours.

The pH of the mixture of crude reaction product and hydroxide solution should be basic, preferably from about 8 to about 11.

In carrying out the process of the present invention, the mixture containing crude reaction product may be heated prior to addition of the aqueous hydroxide solution. It is also possible to first combine the crude reaction mixture and the aqueous hydroxide solution and then heat the resultant mixture to the desired temperature.

The products of the process of the present invention typically have an N-isomer content of less than 2%, preferably about 1% or less.

Having thus described our invention, the following Examples are given as being illustrative thereof. All parts and percentages given in these Examples are parts by weight or percentages by weight, unless otherwise indicated.

EXAMPLES

Metribuzin having an active ingredient content of 91.5%, an N-methyl isomer content of 4% and a moisture content of 4.3% was used in each of Examples 1–11. Metribuzin having an active ingredient content of 91.6%, an N-methyl isomer content of 4.1% and a moisture content of 4.5% was used in each of Examples 12–19.

Examples 1–5

90 g of metribuzin (91.5% A.I., 4% N-isomer, 4.3% moisture) were charged to a reaction vessel. 510 g of mother liquor from the metribuzin production process were also charged into that vessel. Agitation of the contents of the reactor was then begun and continued throughout heating of the contents. 10 g of a 12.5% solution of sodium hydroxide were added over a half hour period. The resultant mixture was heated to the temperature indicated in Table 1 during the addition of the sodium hydroxide solution, for the length of time indicated in Table 1. The resultant product was then cooled and isolated by filtration. The recovered product was dried and analyzed. The results of these analyses are reported in Table 1.

TABLE 1

| EX. | TEMP. (°C.) | TIME[1] (hr.) | PH[2] | PURITY % ACTIVE INGREDIENT | % N-METHYL ISOMER | % NET YIELD |
| --- | --- | --- | --- | --- | --- | --- |
| 1 | 70° | 1.0 | 10.6–10.0 | 98.9 | 0.25 | 94.6 |
| 2 | 65° | 1.0 | 10.7–10.1 | 99.0 | 0.26 | 97.0 |
| 3 | 60° | 1.0 | 10.8–10.2 | 98.7 | 0.42 | 98.7 |
| 4 | 55°[3] | 1.0 | 11.0–10.7 | 96.5 | 2.2 | 96.8 |
| 5 | 60° | 1.0 | 10.8–10.2 | 98.8 | 0.5 | 98.8 |

[1] Does not include 0.5 hour for heating up to reaction temperature.
[2] The first pH is the maximum pH measured during the process. The second value is the pH of the reaction mixture at the termination of the process.
[3] The isomer content could be further reduced by heating for longer periods of time but such extended heating produced a drop in net yield.

Examples 6–8

The procedure of Examples 1–5 was repeated with the same materials with the exception that the temperature at which heating was carried out was maintained at 60° C. and the time the mixture was heated was varied. The results of the analyses of the products thus obtained are reported in Table 2.

TABLE 2

| EX. | COOK TIME | PH[2] | PURITY % ACTIVE INGREDIENT | % N-METHYL ISOMER | % NET YIELD |
| --- | --- | --- | --- | --- | --- |
| 6 | 1.5 hr. | 11.2–10.4 | 98.8 | 0.5 | 98.6 |
| 7 | 1.0 hr. | 10.8–10.2 | 98.8 | 0.45 | 98.5 |
| 8 | 0.5 hr. | 10.5–10.1 | 98.9 | 0.4 | 97.4 |

[2] The first value is the maximum pH reached during the process. The second value is the pH at the termination of heating.

Examples 9–11

The procedure of Examples 1–5 was repeated using the same materials with the exception that the temperature was maintained constant at 60° C. during the reaction and the length of time during which the mixture was maintained at 60° C. was varied. The results of the analyses of the metribuzin thus obtained are reported in Table 3.

TABLE 3

| EX. | TIME (HR.) | PH[2] | PURITY % ACTIVE INGREDIENT | % N-METHYL ISOMER | % NET YIELD |
| --- | --- | --- | --- | --- | --- |
| 9 | 1.0 | 10.8–10.2 | 98.8 | 0.45 | 98.5 |
| 10 | 2.0 | 10.7–10.0 | 99.0 | 0.3 | 96.1 |
| 11 | 3.0 | 10.8–9.8 | 99.1 | 0.15 | 92.8 |

[2] The first value is the maximum pH reached during the process. The second value is the pH at the termination of heating.

Examples 12–16

90.0 g of metribuzin (91.6% A.I., 4.1% N-isomer, 4.5% moisture) were charged to a reaction vessel. 510 g of mother liquor from the metribuzin production process were also charged to this vessel. Agitation of the contents of the vessel was begun and was continued throughout the rest of the process. The contents of the reaction vessel were then heated to 60° C. over a period of 0.5 hours. A 12.5% sodium hydroxide solution was then added in the amount indicated in Table 4. The contents were then heated at a temperature of 60° C. for 1 hour. The heating was then discontinued, the reaction mixture was cooled and the metribuzin recovered by filtration. The recovered metribuzin was then dried and analyzed. The results of these analyses are given in Table 4.

TABLE 4

| EX. | PH[2] | GRAMS OF 12.5% NaOH | PURITY % ACTIVE INGREDIENT | % N-METHYL ISOMER | % NET YIELD |
| --- | --- | --- | --- | --- | --- |
| 12 | 10.4–9.9 | 5 | 96.2 | 2.79 | 99.4 |
| 13 | 10.6–10.2 | 7.5 | 97.3 | 1.64 | 99.1 |
| 14 | 10.7–10.3 | 10.0 | 98.4 | 0.52 | 98.8 |
| 15 | 10.9–10.4 | 15.0 | 98.1 | ≦0.1 | 95.5 |
| 16 | 11.3–10.7 | 20.0 | 99.0 | ≦0.1 | 89.5 |

[2] The first value is the maximum pH measured during the process. The second value is the pH at termination of the process.

Examples 17–19

The procedure used in Examples 12–16 was repeated using the same materials as were used in those Examples with the exception that a 25% NaOH solution was used instead of the 12.5% NaOH solution. The amount of the sodium hydroxide added and the results of the analyses of the product metribuzin are reported in Table 5.

TABLE 5

| EX. | PH[2] | GRAMS OF 25% NaOH | PURITY % ACTIVE INGREDIENT | % N-METHYL ISOMER | % NET YIELD |
| --- | --- | --- | --- | --- | --- |
| 17 | 11.1–10.5 | 5.0 | 98.1 | 1.4 | 96.4 |
| 18 | 11.4–11.0 | 10.0 | 97.5 | ≦0.1 | 87.5 |
| 19 | 11.7–11.3 | 15.0 | 97.3 | 0.1 | 84.1 |

[2]The first value is the maximum pH measured during the process. The second value is the pH measured at termination of the process.

EXAMPLES 20-22

The procedure of Example 1 was repeated using 145 pounds metribuzin having an active ingredient content of 93.9%, an N-isomer content of 4.5% and a moisture content of 1.1%. The amount of 12.5% NaOH was also varied. The amount used in each Example is given in Table 6. The results of the analyses of the product metribuzin are also reported in Table 6.

TABLE 6

| EX. | POUNDS 12.5% NaOH | % N-METHYL ISOMER (INITIAL) | INITIAL % ACTIVE INGREDIENT | % N-METHYL ISOMER (FINAL) | FINAL % ACTIVE INGREDIENT | NET YIELD |
| --- | --- | --- | --- | --- | --- | --- |
| 20 | 13.5 | 4.5 | 93.9 | 0.75 | 97.1 | 98.5 |
| 21 | 14.5 | 4.5 | 93.9 | 0.6 | 97.6 | 98.4 |
| 22 | 15.5 | 4.5 | 93.9 | 0.32 | 98.5 | 98.1 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for removing N-isomers from a reaction product containing a compound represented by the formula

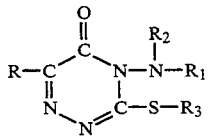

(1)

in which
R represents an alkyl group having from 1–6 carbon atoms, a cycloalkyl group having from 5 to 6 ring carbon atoms, an aralkyl group having from 6 to 10 ring carbon atoms in the aryl moiety and from 1 to 2 carbon atoms in the alkyl moiety, or an aryl group having from 6–10 ring carbon atoms;

$R_1$ and $R_2$ each represents hydrogen, or an alkyl group having from 1 to 4 carbon atoms; and $R_3$ represents an alkyl group having from 1 to 4 carbon atoms by treating the compound represented by formula I at a temperature of from about 55° C. to about 70° C. in the presence of a hydroxide for at least 0.5 hour.

2. The process of claim 1 in which the hydroxide is an alkali metal hydroxide.

3. The process of claim 1 in which the hydroxide is sodium hydroxide.

4. The process of claim 1 in which the compound represented by Formula 1 is heated to approximately 60° C. before the alkali metal hydroxide is added.

5. The process of claim 1 in which the compound represented by Formula I and the hydroxide mixture is maintained at a temperature of approximately 60° C. for from about 1 to about 3 hours.

6. The process of claim 1 in which the mixture of the compound represented by Formula I and the alkali metal hydroxide is maintained at a basic pH while being heated.

7. The process of claim 6 in which the pH is maintained at from about 8.5 to about 10.

8. The process of claim 1 in which the compound represented by Formula I is metribuzin.

9. The process of claim 8 in which the alkali metal hydroxide is sodium hydroxide.

10. The process of claim 9 in which the temperature is maintained at approximately 60° C. for from about 1 to about 3 hours and the pH of the mixture is maintained at a pH of approximately 9.

* * * * *